(12) United States Patent
Kuennecke et al.

(10) Patent No.: US 8,876,732 B2
(45) Date of Patent: Nov. 4, 2014

(54) SAMPLE TAKING DEVICE, AND SAMPLE TAKING METHODS

(75) Inventors: Wolfgang Kuennecke, Braunschweig (DE); Michael Hartlep, Braunschweig (DE); Jens Giesenberg, Wolfenbüttel (DE); Matthias Lehmann, Braunschweig (DE)

(73) Assignee: Trace Analytics GmbH, Braunschweig (DE)

( * ) Notice: Subject to any disclaimer, the term of this patent is extended or adjusted under 35 U.S.C. 154(b) by 1323 days.

(21) Appl. No.: 12/515,378

(22) PCT Filed: Nov. 16, 2007

(86) PCT No.: PCT/EP2007/062449
§ 371 (c)(1),
(2), (4) Date: Dec. 24, 2009

(87) PCT Pub. No.: WO2008/059050
PCT Pub. Date: May 22, 2008

(65) Prior Publication Data
US 2010/0113975 A1 May 6, 2010

(30) Foreign Application Priority Data
Nov. 17, 2006 (EP) .................................. 06124342

(51) Int. Cl.
*A61B 5/00* (2006.01)
*B65D 81/00* (2006.01)
(Continued)

(52) U.S. Cl.
CPC ............ *A61B 5/1459* (2013.01); *B01D 61/243* (2013.01); *G01N 21/82* (2013.01); *A61B 5/686* (2013.01); *G01N 2021/7786* (2013.01); *A61B 5/6852* (2013.01); *A61B 5/14528* (2013.01); *A61B 5/14539* (2013.01); *A61B 5/14532* (2013.01)
USPC ........ 600/573; 600/578; 600/579; 210/321.6; 210/646; 427/2.3; 604/29

(58) Field of Classification Search
USPC .............. 600/573, 578, 579; 427/2.3; 604/29; 210/321.6, 646
See application file for complete search history.

(56) References Cited

U.S. PATENT DOCUMENTS 4,265,249 A * 5/1981 Schindler et al. ............. 600/573
4,694,832 A 9/1987 Ungerstedt
(Continued)

FOREIGN PATENT DOCUMENTS

DE 19714572 6/1998

*Primary Examiner* — Devin Henson
(74) *Attorney, Agent, or Firm* — Duane Morris LLP; J. Rodman Steele, Jr.; Gregory M. Lefkowitz

(57) ABSTRACT

Sampling device for obtaining a sample of an analyte, comprising a feed line (30) and a discharge line (40) as well as an analyte feed chamber (13) in fluidic connection between the feed line and the discharge line, the analyte feed chamber having an opening (14) which is provided with an analyte-permeable membrane (15) to allow the analyte to pass through from a region outside the analyte feed chamber into the analyte feed chamber, the surface area of the opening of the analyte feed chamber being at most 400 times the minimum cross-sectional surface area of the discharge line, more preferably at most 100 times and most preferably 50 to 80 times the minimum cross-sectional surface area of the discharge line. This device will reduce the dead time between the passage of the analyte through the membrane and the detection of said analyte at the sensor.

22 Claims, 7 Drawing Sheets

(51) Int. Cl.
*B01D 63/00* (2006.01)
*C02F 1/44* (2006.01)
*B01D 11/00* (2006.01)
*B01D 61/00* (2006.01)
*A41D 19/00* (2006.01)
*B05D 3/00* (2006.01)
*A61M 1/00* (2006.01)
*B01D 61/24* (2006.01)
*A61B 5/145* (2006.01)
*A61B 5/1459* (2006.01)
*G01N 21/82* (2006.01)
*G01N 21/77* (2006.01)

(56) References Cited

U.S. PATENT DOCUMENTS

| | | | |
|---|---|---|---|
| 7,111,503 B2 * | 9/2006 | Brumboiu et al. | 73/64.56 |
| 7,510,654 B2 * | 3/2009 | Mir et al. | 210/321.6 |
| 2001/0015253 A1 * | 8/2001 | Liska et al. | 156/244.13 |
| 2005/0160801 A1 | 7/2005 | Brumboiu | |
| 2010/0204565 A1 * | 8/2010 | Falken et al. | 600/424 |

* cited by examiner

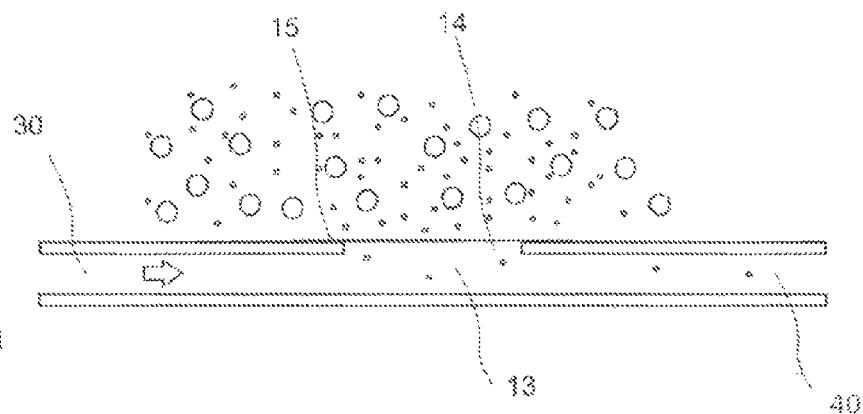
Fig. 1a
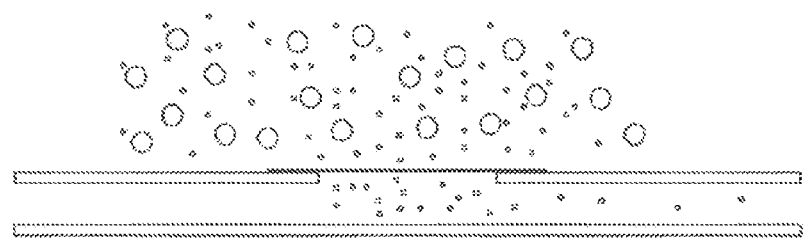
Fig. 1b
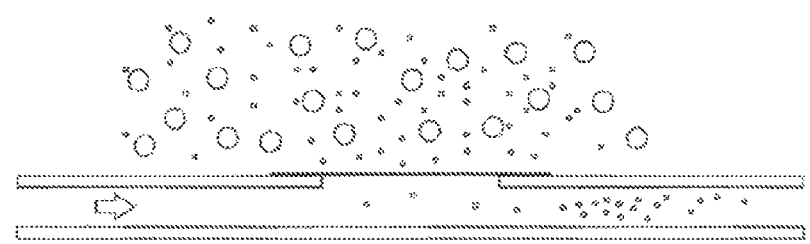
Fig. 1c
Fig. 1

SAMPLE TAKING DEVICE, AND SAMPLE TAKING METHODS

CROSS-REFERENCE TO RELATED APPLICATIONS

This application is a §371 national stage entry of International Application No. PCT/EP2007/062449, filed Nov. 16, 2007, which claims priority to EP 06124342.4, filed Nov. 17, 2006, both of which are hereby incorporated by reference in their entirety.

BACKGROUND OF THE INVENTION

The present invention relates to a sampling device for obtaining a sample of an analyte, and to a method for obtaining a sample of an analyte.

In process engineering and medicine, in particular when observing a bioreactor and during the long-term determination of the content of preselected substances in the human body, it is often necessary to rapidly determine as continuously as possible the presence and, if necessary, the concentration of a preselected analyte in a medium. In this respect, it is often impossible for hygiene and/or medical reasons to directly take material of the medium to be examined, for example in a biopsy, in a repeated or continuous manner. For this reason, a sample of the analyte is usually obtained from the medium by a dialysis process. In such a process, a probe provided with a dialysis or gas diffusion membrane as the "measuring window" is introduced into the medium to be examined and is optionally implanted for a relatively long time. The probe is flushed continuously or in pulses with a transport medium. The analyte passes through the membrane into the transport medium of an analyte feed chamber positioned after the membrane in the analyte flow direction and is transported through the probe through a probe outlet out of the region of the medium to be examined, in particular a bioreactor or a human or animal body. The transport medium which may be loaded with analyte can then be analyzed by one or more sensors. Examples of such probes and associated sampling methods are described in DE 44 26 694, U.S. Pat. No. 3,640,269, U.S. Pat. No. 4,694,832, U.S. Pat. No. 6,632,315 B2, U.S. Pat. No. 6,811,542 B2, WO 99/45982 A2 and WO 01/06928 A1.

A problem of previous probes and of corresponding sampling methods was the restricted transportation speed of the analyte in the probes and accordingly the lengthy dead time between the first passage of the analyte through the membrane and the first detection of the analyte at the probe outlet. For example, the cardiac catheter described in WO 99/45982 A2 requires a dead time of 15 to 20 minutes before a measurable signal is present; more on this below.

To solve this problem, it was attempted on the one hand to increase the membrane surface area. For this purpose, microdialysis probes, for example were used which comprise hollow fibers with an individual fiber diameter of approximately 500 µm. A disadvantage here is that when the probe is withdrawn, particularly from tissue, the membrane can become detached and can remain in the body. To achieve a high transportation speed, microdialysis probes are often charged with a high internal pressure of the transport medium. The high internal pressure also stresses the connections between the hollow fibers and the rest of the probe, so that tears often appear in the hollow fibers or the hollow fibers tear out of the probe.

In addition, the pressure fluctuations which may occur during conventional operation of a bioreactor or during implantation of a probe in a human or animal patient body give rise to strong fluctuations in the dialysis rate. This effect is further intensified in that the used membrane materials swell considerably in aqueous surroundings and consequently become very flexible. Thus, when hollow fibers are used, after implantation or immersion into a measuring solution, "tubular bags" which are very pulsatable are produced as measurement windows. The dialysis rate then fluctuates considerably because the membrane cell volume can constantly change internally with a varying counter pressure. Even the smallest movements or fluctuations in pressure can be clearly detected. A remedy can only be provided by operation under elevated internal pressure, which again increases the risk of rupture. Accordingly, such microdialysis probes are generally unsuitable for a pulse-wise loading of the probe with the transport medium.

The cylindrical dialysis chambers which result when hollow fibers are used suffer from disadvantages from a fluid-dynamics point of view as well. Produced in the analyte feed chamber are regions, corners and reversals in direction which are flown through in different ways depending on construction and in which air bubbles can be deposited. Since microdialysis probes usually comprise analyte feed chambers of a small internal diameter, only slow flow rates can build up inside, so that it is very difficult to flush out the air bubbles. The air bubbles alter the volume of the analyte feed chamber filled with transport medium and/or the effective membrane surface area and thus give rise to considerable measurement errors.

And finally, the maximum volume flow of the transport medium in a microdialysis probe is restricted due to the desirable high substance transportation rate of the analyte into the analyte feed chamber. Conventional microdialysis probes can only be operated at transport medium volume flows of 0.3-0.5 µl/min. Thus, for the transportation of the transport medium out of the analyte feed chamber to the probe outlet, with an assumed transportation path of 30 cm and a conventional probe internal diameter of 75 µm, a time (dead time) of 160 s is required and with a probe internal diameter of 150 µm, a time of even 630 s is required. By reducing the probe internal diameter, the pressure of the transport medium at the same transportation speed increases by a factor of 4, so that a minimum internal diameter of the probe must be observed to prevent the membrane from tearing or bursting.

Sampling probes are also known in which the transport medium is not exchanged continuously but in pulses. In this case, the analyte diffuses out of the medium to be investigated also through a membrane (dialysis or gas diffusion membrane) into an analyte feed chamber positioned after the membrane in the diffusion direction, into the transport medium. Depending on the length of time between two consecutive transport medium exchange pulses, the analyte is concentrated to different degrees with the same starting analyte concentration of the medium to be examined in the analyte feed chamber. For example, U.S. Pat. No. 6,852,500 describes a microdialysis probe and a glucose flow sensor, a transport medium flowing in pulses through the microdialysis probe. Bearing in mind the internal volume of the microdialysis probe, there results a period of 9 minutes until the entire volume of the analyte feed chamber has passed through the probe outlet and has reached the glucose flow sensor. The measured results determined thus can therefore only be averages and merely reflect the actual course of the glucose concentration in a time-delayed and damped-down manner.

Therefore, the object of the present invention was to provide a sampling device by which the disadvantages described above of conventional sampling devices can be avoided or reduced. The sampling device should in particular allow a short dead time between the entering of an analyte into an analyte feed chamber and passage through the sampling device outlet. A transport medium should preferably be able to flow through a course 30 cm in length between the analyte feed chamber and the sampling device outlet within 2 minutes, without pressures arising which can threaten the reliable operation of the sampling device and in particular initiate tearing of the sampling device. Furthermore, a corresponding sampling method is provided.

The object is achieved by a sampling device according to claim 1. Advantageous developments of the invention are described in the subclaims. A sampling method is described in claim 17.

DETAILED DESCRIPTION

According to the invention, a sampling device for obtaining a sample of an analyte comprises a feed line and a discharge line as well as an analyte feed chamber in fluidic connection between the feed line and the discharge line. The analyte feed chamber has an opening which is provided with an analyte-permeable membrane to allow the analyte to pass through from a medium to be investigated from a region outside the analyte feed chamber ("outside") into the analyte feed chamber. The sampling device according to the invention is characterized in that the surface area of the opening of the analyte feed chamber is at most 400 times, preferably at most 200 times and more preferably 40-80 times the minimum cross-sectional surface area of the discharge line. In this respect, the expression "minimum cross-sectional surface area of the discharge line" is understood as meaning the surface area of the cross section which is the smallest for the discharge line and the analyte feed chamber inside the sampling device. The minimum cross-sectional surface area usually acts in a manner restricting the throughflow amount. The expression "surface area of the opening" is understood as meaning the surface area which most greatly restricts the passage of the analyte from outside into the analyte feed chamber. The surface area will usually be the surface area of the window-like passage opening of the sampling device. However, instead of consisting of a single window, the surface area can also consist of a large number of windows which in cooperation collectively produce one opening in the analyte feed chamber in the direction of the medium to be investigated. The surface area of the opening is then the overall surface area of the individual windows. It is possible to choose any form of the opening (as a single window or as a large number of windows). In making this choice, a person skilled in the art will particularly consider the effects of the opening geometry on the stability of the sampling device according to the invention.

Surprisingly, it has been found that it is still possible to obtain a measurable analyte signal at the end of the discharge line of the sampling device with the small opening, compared to conventional sampling devices, provided according to the invention. This was surprising because it was to be expected that a small opening would allow only a slow diffusion of the analyte into the analyte feed chamber, the concentration of the analyte in the analyte feed chamber would accordingly be low per unit of time and due to the turbulence-induced dilution during transportation of the analyte from the analyte feed chamber through the discharge line, a signal would be obtained at the end of the discharge line which would barely still be measurable. In fact, it has been found that although a dilution takes place during transportation of the analyte through the discharge line, since the analyte was originally concentrated in only a small volume in the diffusion direction after the small opening, this dilution turns out to be low. Furthermore, the opening of the analyte feed chamber which is small compared to the minimum cross-sectional area makes it possible to charge the analyte feed chamber with a high volume flow of the transport medium, without the fear that the membrane will tear. The high volume flow can prevent the deposit of bubbles in the analyte diffusion direction after the membrane in the analyte feed chamber; this additionally and simply increases the measuring reliability.

In preferred embodiments of the sampling device according to the invention, the length of the discharge line, measured from the edge of the opening of the analyte feed chamber to the end of the discharge line
a) is at least 20 cm, preferably 30 cm to 80 cm and more preferably 35 cm to 50 cm, or
b) is 3 to 15 cm, preferably 5 to 10 cm and more preferably 6 to 8 cm.

The measurements described in a) are particularly suitable for central venous catheters and comparable sampling probes, while the measurements described in b) are particularly suitable for indwelling catheters.

With these lengths of the discharge line and thus of the analyte transport paths, the turbulence-induced dilution of the analyte remains within limits which make it possible to determine the concentration of conventional analytes, such as glucose from an implanted catheter in a human or animal.

In preferred embodiments, the minimum cross-sectional surface area of the discharge line of a sampling device according to the invention is
a) 0.1 to 0.8 $mm^2$ and more preferably 0.2 to 0.5 $mm^2$, or
b) 0.008 to 0.8 $mm^2$, preferably 0.018 to 0.5 $mm^2$ and more preferably 0.03 to 0.2 $mm^2$.

Again, the minimum cross-sectional surface areas described in a) are particularly suitable for central venous catheters, while the minimum cross-sectional surface areas described in b) are particularly suitable for indwelling catheters due to the overall relatively small size.

Furthermore, it is beneficial to select the volume of the analyte feed chamber as a function of the surface area of the opening of the analyte feed chamber. The ratio between opening surface area and analyte feed chamber volume, particularly for central catheters, is preferably 20 $mm^2/15$ $mm^3$ to 45 $mm^2/15$ $mm^3$, more preferably 25 $mm^2/15$ $mm^3$ to 38 $mm^2/15$ $mm^3$ and most preferably 30 $mm^2/15$ $m^3$. In conventional microdialysis devices, the ratio is significantly greater and is frequently approximately 16 $mm^2/2$ $mm^3$. This entails a drawn-out "grafting" of the analyte in the transport medium which is pulled apart even more during transportation and thus requires considerably more time for a complete measurement than with a sampling device according to the invention.

In preferred embodiments of the invention, the membrane of a sampling device according to the invention has an exclusion limit of 80 kDa, preferably 60 kDa and more preferably 20 kDa. Thus, the membrane of a sampling device according to the invention is passable for small analytes, as are usually of interest particularly during examination of a human or animal patient. Analytes which are of interest and correspondingly derived variables which can be determined using a sampling device according to the invention are preferably glucose, lactate, pH, $pO_2$ and $pCO_2$, methanol, ethanol, formiate, acetate, glutamine, glutamate, urea, uric acid, phosphate, antibodies, growth factors and hormones. Accordingly, the membrane material is preferably selected from the group consisting of cellulose and derivatives thereof, cellulose acetate, PTFE, polycarbonate, polypropylene, polyamides, polysulfones, a cellulose-acetate membrane being particularly preferred for detecting glucose.

The sampling device according to the invention preferably further comprises a line for a further medium flow which is different from the transport medium. In preferred embodiments, the further line opens out during use into the medium to be investigated. In this way, simultaneously with a sampling of a medium surrounding the sampling device, it is possible to introduce a medium flow into or remove said medium flow from this medium. In this respect, a particularly preferred embodiment comprises an opening which connects the analyte feed chamber to the line of the further medium flow, in which case optionally no opening is provided to the medium which is outside the sampling device. A sampling device of this type can be used, for example to introduce a calibrating solution via the opening to calibrate the sampling device, in which case for investigating the medium which is outside the sampling device, this medium is then drawn up by suction into the line. The introduction of a calibrating solution or other infusion solution and the drawing-up by suction of the medium to be investigated can be performed by a pump, preferably in regular intervals. Consequently, the exposure of the opening with respect to the medium to be investigated can be controlled.

In a further embodiment, the sampling device according to the invention comprises two openings, one of which is connected to the medium to be investigated during intended use and the other is connected to the further line. In this way for example the analyte in the analyte feed chamber can be diluted.

The further line can, however, also be separated from the medium to be investigated. This allows a more accurate calibration through the analyte feed chamber.

The further line can also be provided with additional sensors, for example fiber optics for measuring oxygen or pH value. For this purpose, optical waveguides are used the tip of which is coated, for example with an indicator dye and which changes in fluorescence, for example, as a function of the concentration of the surrounding analyte.

The sampling device according to the invention is preferably a sampling catheter, preferably for a blood test in the form of an intravenous cannula, and more preferably a central venous catheter for use in a mammal, particularly a human. Sampling devices according to the invention are also preferred in the form of a bioreactor probe.

The feed line and discharge line in the sampling device according to the invention are preferably contained next to one another in a uniform structure. This arrangement is particularly useful in medical sampling devices, particularly in the form of central venous catheters and indwelling cannulas.

The sampling device according to the invention is preferably connected to a detector for detecting the analyte. It is also preferred to connect the sampling device to a pump for pumping a transport medium through the feed line and/or discharge line of the sampling device. The discharge line of the sampling device is expediently fluidically connected to the detector, optionally via the pump.

If the sampling device is provided with a pump, in preferred embodiments the pump has a controller for actuating the pump at a preselected time. The pump can thus be switched on and off, particularly at preselected times, such that the transport medium flows through the sampling device in pulses. The controller is more preferably configured such that the pump is switched off for 20 to 90 seconds, preferably for 30 seconds so that analyte can pass through the membrane into the analyte feed chamber, and is then switched on long enough for the analyte-loaded carrier medium volume to be pumped out of the analyte feed chamber through the discharge line out of the sampling device and preferably pumped into a detector. In the case of an analyte feed chamber 10 to 20 mm$^3$ in size, it is preferred to switch off the pump for 20 to 90 seconds. It is further preferred to provide between the pump and the feed line and/or discharge line a flow interrupter with a controller such that the flow of transport medium through the feed line and discharge line can be stopped and started independently of the operation of the pump. The flow interrupter then functions like a pump which is switched on and off at preselected times, but the pump does not have to be switched off.

A sampling device is particularly preferred in which the feed and discharge lines are connected to the detector via a distributor such that for flushing purposes, a transport medium can be passed to the detector from the distributor without passing through the analyte feed chamber, and for measuring purposes the transport medium can be passed from the distributor to the detector while passing through the analyte feed chamber.

This embodiment of the sampling device according to the invention utilizes in a particularly advantageous manner the fact that the detector can be flushed in the time required for loading the resting transport medium in the analyte feed chamber with analyte. Thus, this sampling device according to the invention makes it possible for a rapid sequence of measurements to be carried out without transport medium used for flushing having to pass through the analyte feed chamber and optionally having to be loaded with minimum quantities of the analyte, which could result in a miscalibration of the detector.

BRIEF DESCRIPTION OF THE DRAWINGS

FIGS. 1a-c show the sampling process using a sampling device as described herein.

DETAILED DESCRIPTION

Figure 19:
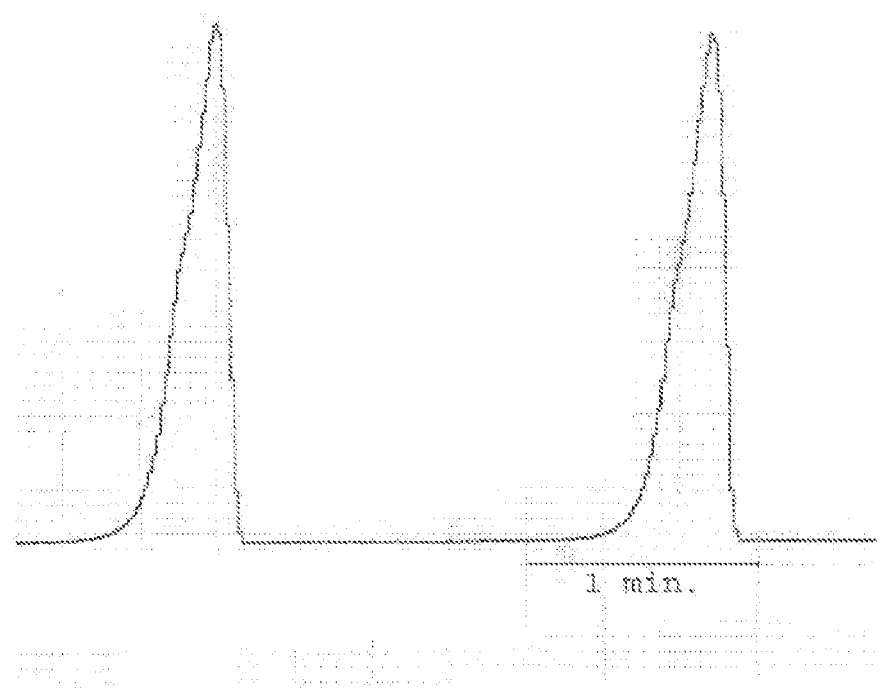
FIG. 19 is a graph showing the signal dependence of glucose concentration versus time.

The invention will be described in detail in the following with reference to the Figures and examples, without these restricting the scope of protection of the claims:

FIG. 1 schematically shows the sampling process. In the starting state, transport solution is conveyed through the feed chamber 13 (FIG. 1a). In so doing, a small amount of analyte continuously passes through the membrane 15 into the feed chamber and is immediately further transported to the discharge 40. For concentration purposes, the transport solution is stopped for a certain time so that a greater amount of analyte can accumulate in the feed chamber (FIG. 1b). The transport flow is then restarted and the accumulated amount of analyte is further transported to the discharge (FIG. 1c). During this procedure, a concentration of analyte is formed which generates a peak-like signal, as shown in FIG. 19, in a detector connected downstream. The height, area or initial gradient can then be used to determine the concentration of analyte.

Example 1

Central Venous Catheter

Central venous catheters have been routinely used hitherto for infusion. Central venous catheters according to the invention are shown in FIGS. 2 to 12. The catheters can either be configured only for dialysis (FIGS. 2 to 11) or as multipurpose catheters. For multipurpose catheters, it is possible to realize the most varied catheter cross sections, for example one or two measuring ducts with two infusion ducts. In addition, further ducts can be provided for motion wires or for introducing fiber optic sensors, for example.

The catheters 10 according to the invention have a feed line 30 and a discharge line 40. They are substantially tubular. An opening 14 is provided in one side of the catheter 10. The opening 14 is covered or filled with a membrane 15. The space 13 in the discharge line 40 which extends over the length of the opening in the main extension direction of the catheter 10 forms an analyte feed chamber. During operation, the analyte feed chamber is filled with a transport medium for an analyte (not shown) which diffuses through the membrane 15 into the analyte feed chamber.

Figure 2:
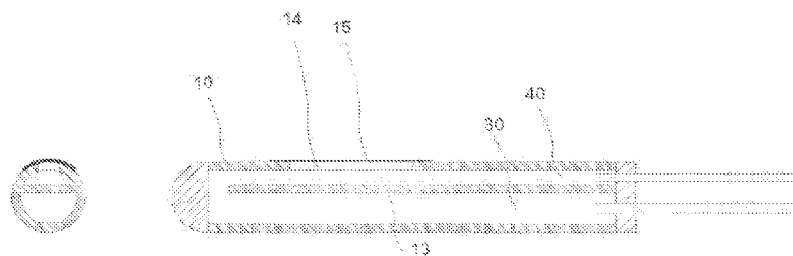
FIG. 2 shows a sampling device with an opening tightly sealed by a membrane.

In the construction shown in FIG. 2, a piece of membrane 15 is applied externally onto the catheter surface such that the opening 14 is tightly sealed by the membrane. If different lumen cross sections of the discharge line 40 are used, the smaller cross section is to be used for removing the signal (outlet).

Figure 3:
FIG. 3 shows a sampling device with a tubular membrane over an opening.
Figure 4:
FIG. 4 shows a sampling device of FIG. 2 with a sock covering the tip of the catheter.
Figure 5:
FIG. 5 shows a sampling device of FIG. 3 with a sock covering the tip of the catheter.

In the embodiment according to FIG. 3, a membrane 15 is positioned as a tube from the outside over the catheter 10 and is bonded, fused or attached in a fluid-tight manner by another means such that the analyte can diffuse into the analyte feed chamber, but transport medium cannot exit through the opening.

In a further embodiment, in addition to the membrane known from FIG. 3, a further layer 16 in which the window over the opening 14 is left free, is fitted over the catheter. This prevents the edges of the membrane from being damaged when the catheter is inserted into or removed from a patient's body. The further layer can enclose the entire point of the catheter like a sock (FIGS. 4 and 5) or can leave the catheter tip free in the manner of a tube (not shown).

Figure 6:
FIG. 6 shows a sampling device of FIG. 2, except with round internal chambers.
Figure 7:
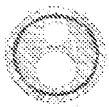
FIG. 7 shows a sampling device of FIG. 5 except with round internal chambers.
Figure 7:
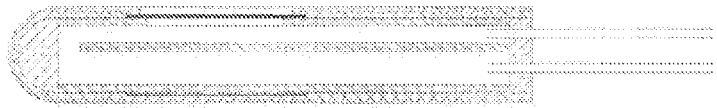
Figure 8:
FIG. 8 shows a sampling device of FIG. 6, except that the membrane is located within the analyte feed chamber.
Figure 8:
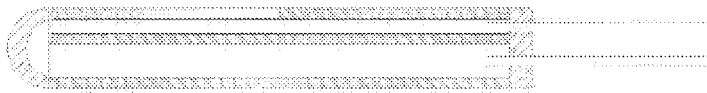

The inner lumen of the analyte feed chamber can be configured in any manner. While the sampling devices according to FIGS. 2 to 5 have a D-shaped cross section of the analyte feed chamber, the cross section in the catheters according to FIGS. 6 to 8 is round. The catheter according to FIG. 6 otherwise corresponds to that of FIG. 2 and the catheter according to FIG. 7 otherwise corresponds to that of FIG. 5.

Figure 9:
FIG. 9 shows a sampling device of FIG. 2, except that the membrane is located within the analyte feed chamber.
Figure 9:
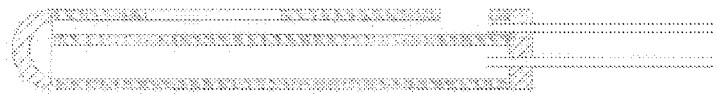
Figure 10:
FIG. 10 shows another embodiment of the sampling device with an internal cavity into which a generally cylindrical feed line is inserted.
Figure 10:

FIG. 8 shows a catheter in which the membrane 15 is not arranged on the outside of the catheter, but on the inside of the analyte feed chamber with a round cross section. FIG. 9 shows a corresponding catheter with a D-shaped cross section. FIG. 10 shows a catheter according to the invention of the type shown in FIG. 8, the cross section of the analyte feed chamber being circular.

Figure 11:
FIG. 11 shows a variation of the sampling device in FIG. 10 where the feed line includes spacers.
Figure 11:

The analyte feed chamber of the catheter according to FIGS. 2 to 9 was formed as a recess in a substantially cylindrical hollow body, the feed line 30 and discharge line 40 having a common wall formed integrally from the rest of the catheter. FIGS. 10 and 11 show alternative catheters according to the invention, in which the substantially cylindrical catheter comprises an inner cavity into which a tube is inserted which serves as the feed line 30. Part of the tube is distanced from the wall of the inner cavity of the catheter and thus forms a free space. The free space is in connection with the discharge line 40. As is conventional in the previous Figures, the catheter is provided with a window to allow the entrance of the analyte. The window is covered by a membrane on the wall of the inner cavity of the catheter to prevent the transport medium from escaping out of the window. Transport medium can issue into the free space in the inner cavity of the catheter via the tube of the feed line 30, an analyte to be examined can enter the inner cavity of the catheter through the window and the membrane and can be concentrated in the transport medium in the analyte feed chamber located in the entry direction after the window. The transport medium can then be diverted through the discharge line 40 and supplied to a sensor (not shown).

The catheter according to FIG. 11 differs from that according to FIG. 10 in that the tube serving as the feed fine 30 has spacers on its outer wall.

Furthermore, in addition to or as an alternative to the tube serving as the feed line 30, the discharge line 40 can also be provided with a tube. Such an embodiment is shown in FIG. 11.

Figure 12:
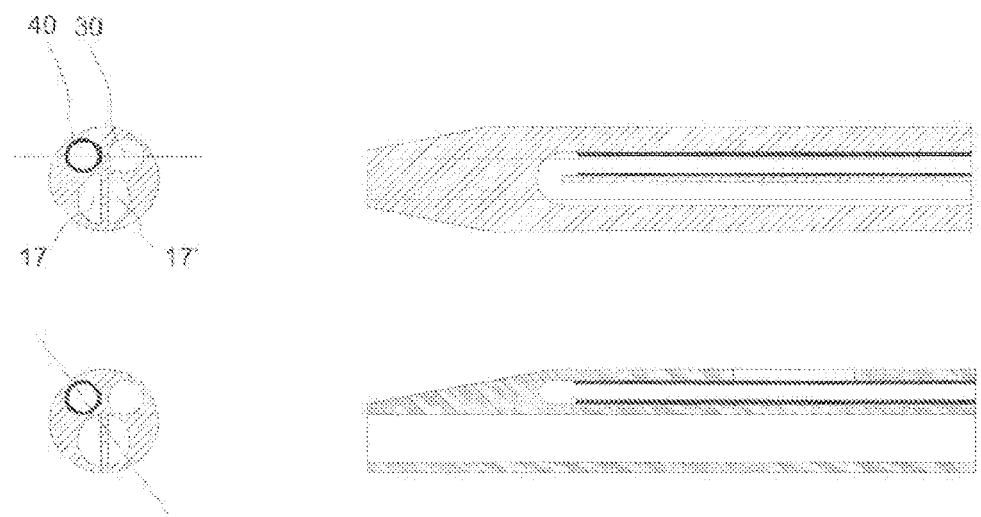
FIG. 12 shows a sampling device as described herein that includes a feed line, a discharge line, and a tubular recess provided as an infusion line.

A sampling device according to the invention can comprise further constituents apart from those shown in FIGS. 1 to 11. For example, FIG. 12 shows a catheter according to the invention which, in addition to a feed line 30 and a discharge line 40, also comprises an additional tubular recess 17/17' which extends up to the tip of the catheter. The further recess is provided as a line for an infusion, as is usual for a conventional catheter. It is configured in two parts and thus allows the separate conduction of two streams of fluid into or out of a human or animal patient body which is to be examined.

Figure 13:
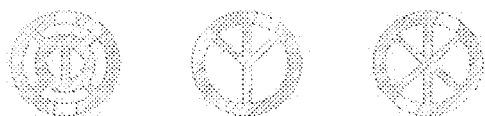
FIG. 13 shows a variety of cross-sections for sampling devices, such as that shows in FIG. 12, that include a feed line, a discharge line, and a tubular recess provided as an infusion line.

Further alternative cross sections of sampling devices according to the invention are shown in FIG. 13.

Example 2

Indwelling Cannulas

Indwelling cannulas, also known as Braunula IV cannulas, are frequently used in infusion therapy. They are inserted into small peripheral veins, for example on the hand or foot. They are usually used for the infusion of solutions and for frequent taking of blood samples. Thus, Braunula IV cannulas are for the most part smaller, shorter and thinner than central venous catheters.

To apply an indwelling cannula, first of all, a needle arranged in the lumen of the cannula pierces the skin of a patient and the vessel to be treated. The needle is then slowly removed and an overlying flexible plastics material part is introduced into the vein.

Figure 14:
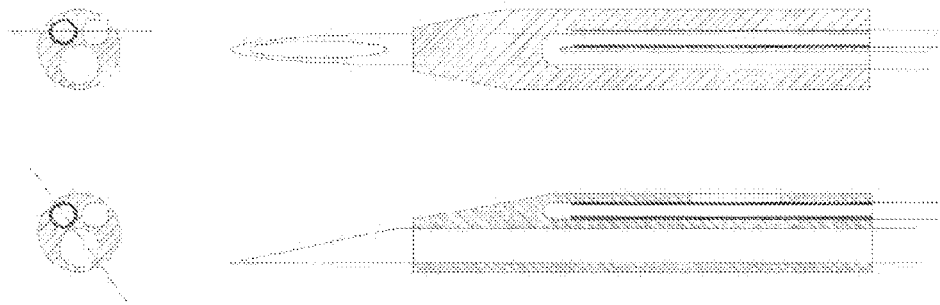
FIG. 14 shows a sampling device that includes a feed line, a discharge line, and a tubular recess receiving a needle and an opening connecting the feed line (analyte feed chamber) with the exterior of the device.
Figure 15:
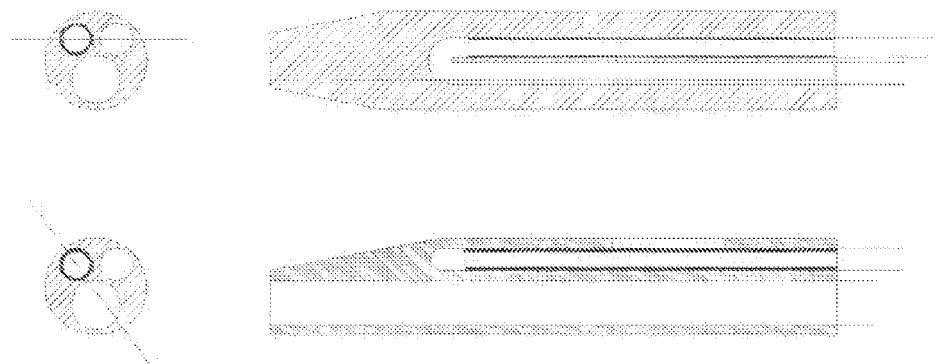
FIG. 15 shows a sampling device of FIG. 14 without a needle.
Figure 16:
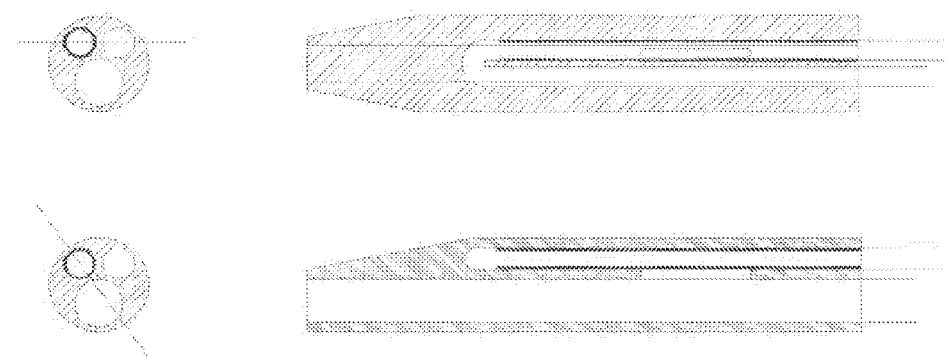
FIG. 16 shows a sampling device similar to that of FIG. 14 except with an opening connecting the analyte feed chamber to the tubular recess.
Figure 17:
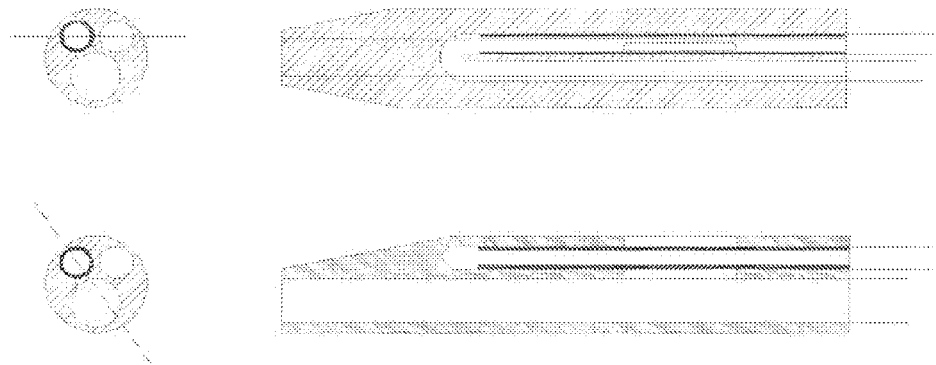
FIG. 17 shows a sampling device similar to that of FIG. 16 except that it includes a second opening connecting the analyte feed chamber with the exterior of the device.
Figure 18:
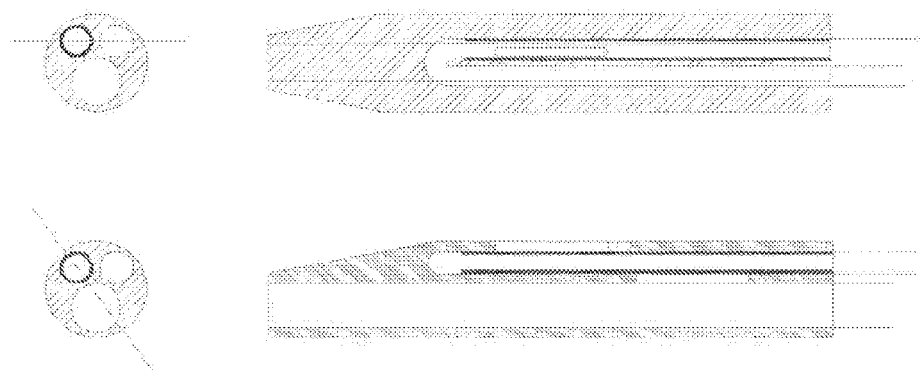
FIG. 18 shows a sampling device similar to that of FIG. 17 except that the opening and the second opening are offset from one another.

FIGS. 14 to 18 show embodiments of indwelling catheters according to the invention each in a plan view and a side view. The catheters have a construction of the type shown in FIG. 12, the recess which extends to the tip of the catheter being configured to receive the needle used for the application. FIG. 14 shows a corresponding catheter with a needle, while FIG. 15 shows a catheter without a needle. FIG. 16 shows a further catheter without a needle and in this case the opening 14 is not positioned on the outside of the catheter, but connects the recess extending to the tip of the catheter to the analyte feed chamber. An arrangement of this type of the opening 14 makes it possible to sample a medium located in the inner recess. FIGS. 17 and 18 show a further embodiment of the type shown in FIG. 16. This embodiment also comprises a further opening 14 to connect the analyte feed chamber to a medium located outside the catheter. The two openings can be arranged opposite one another (FIG. 17) or offset with respect to one another (FIG. 18).

Example 3

Use of a Sampling Device According to the Invention

A conventional double D catheter having an external diameter of 1.6 mm was provided with a membrane-covered opening of 30 mm$^2$ (1.5 mm×20 mm rectangular, width×length) corresponding to FIG. 2. The catheter was immersed with its opening into an aqueous glucose solution. A transport medium consisting of 100 mM potassium phosphate buffer solution, pH 7.5 was conveyed for 60 s at 1.5 ml/min through the feed and discharge lines. The transport medium was then not conveyed for 30 seconds through the feed and discharge lines, so that analyte could pass through the membrane into the analyte feed chamber during this time. Positioned at the outlet of the catheter was a flow sensor with an immobilized glucose-oxidase electrode. The distance between the opening and the flow sensor was 100 cm. All investigations were carried out at room temperature. The transport medium which was conveyed into the flow sensor and optionally contained glucose was measured using an amperometric measuring amplifier at a potential of 350 mV. The signals which resulted had a distinct peak form. FIG. 19 shows the signal dependence (peak maximum) in respect of the glucose concentration of the glucose solution. The total passage time per measurement signal was less than 60 seconds. The calibration straight line passes through the origin, so that single point calibrations, for example by means of external measuring devices are possible.

We claim:

1. Sampling device for obtaining a sample of an analyte, comprising a feed line and a discharge line as well as an analyte feed chamber in fluidic connection between the feed line and the discharge line, the analyte feed chamber having an opening which is provided with an analyte-permeable membrane to allow the analyte to pass through from a region outside the analyte feed chamber into the analyte feed chamber, wherein
   a surface area of the opening of the analyte feed chamber is at most 400 times the minimum cross-sectional area of the discharge line,
   a cross sectional area which is smallest for the discharge line and the analyte feed chamber inside the sampling device is 0.001 to 0.8 mm$^2$, and
   a ratio between the surface area of the opening and an analyte feed chamber volume ranges from 20 mm$^2$/15 mm$^3$ to 45 mm$^2$/15 mm$^3$.

2. Sampling device according to claim 1, wherein the length of the discharge line, measured from the edge of the opening of the discharge line,
   a) is at least 20 cm, or
   b) is 3 to 15 cm.

3. Sampling device according to claim 1, wherein the minimum cross-sectional surface area of the discharge line is
   a) 0.1 to 0.8 mm$^2$ for a venous sampling device, or
   b) 0.008 to 0.8 mm$^2$ for an indwelling sampling device.

4. Sampling device according to claim 1, wherein the surface area of the opening of the analyte feed chamber is 0.05 to 100 mm$^2$.

5. Sampling device according to claim 1, wherein the ratio between the surface area of the opening and the analyte feed chamber volume ranges from 25 mm$^2$/15 mm$^3$ to 38 mm$^2$/15 mm$^3$.

6. Sampling device according to claim 1, wherein the membrane has an exclusion upper limit of 80 kDa.

7. Sampling device according to claim 1, wherein the membrane consists of a material selected from the group consisting of cellulose and the derivatives thereof, cellulose acetate, PTFE, polycarbonate, polypropylene, polyamides and polysulfones.

8. Sampling device according to claim 1, wherein the membrane is attached by adhesive methods, by sheathing with the material, casting or by lithographic polymerization of the surrounding structure.

9. Sampling device according to claim 1, wherein the sampling device is a sampling catheter.

10. Sampling device according to claim 1, wherein the feed line and the discharge line are contained in the sampling device next to one another in a uniform structure.

11. Sampling device according to claim 1, further comprising a detector for detecting the analyte.

12. Sampling device according to claim 11, wherein the feed line and discharge line are connected to the detector via a distributor such that
   for flushing purposes, a transport medium can be passed from the distributor to the detector without passing through the analyte feed chamber, and
   for measuring purposes, the transport medium can be passed from the distributor to the detector while passing through the analyte feed chamber.

13. Sampling device according to claim 1, wherein the sampling device is further provided with a pump for pumping a transport medium through the feed line or discharge line.

14. Sampling device according to claim 13, wherein the discharge line is fluidically connected to a detector for detecting an analyte.

15. Sampling device according to claim 13, further comprising a controller for actuating the pump at a preselected time.

16. Sampling device according to claim 1, also comprising a further opening in the analyte feed chamber which is provided with an analyte-permeable membrane, and a pump for charging the further opening with a medium for adjusting an analyte concentration in the analyte feed chamber.

17. Method for determining an analyte in a medium, comprising the steps:
   a) introducing an analyte feed chamber of a sampling device according to claim 1 into the medium to be analyzed;
   b) before, during or after step a), filling the analyte feed chamber with a transport medium for receiving the analyte;
   c) transporting the transport medium out of the analyte feed chamber through the discharge line of the sampling device to a detector; and
   d) determining the analyte in the discharged transport medium by means of the detector.

18. The sampling device according to claim 1, wherein the surface area of the opening of the analyte feed chamber is at most 100 times the minimum cross-sectional surface area of the discharge line.

19. The sampling device according to claim 1, wherein the length of the discharge line, measured from the edge of the opening of the discharge line,
   a) at least 30 cm, or
   b) 5 to 10 cm.

20. The sampling device according to claim 1, characterized in that the minimum cross-sectional surface area of the discharge line is
   a) 0.2 to 0.5 $mm^2$ for a venous sampling device, or
   b) 0.018 to 0.5 $mm^2$ for an indwelling sampling device.

21. The sampling device according to claim 1, further comprising a third fluid line for a separate fluid medium flow, wherein analyte can pass from the third fluid line to the analyte feed chamber through the analyte-permeable membrane.

22. The sampling device according to claim 21, further comprising a pump to draw a fluid medium to be investigated from outside the device up into the third fluid line to expose the fluid to the opening of the analyte feed chamber.

* * * * *